United States Patent [19]
Lachmann et al.

[11] Patent Number: 5,738,090
[45] Date of Patent: Apr. 14, 1998

[54] RESPIRATORY SYSTEM FOR DETERMINING AN OPENING PRESSURE OF A LONG SYSTEM AND MAINTAINING THE LUNG SYSTEM OPEN

[75] Inventors: Burkhard Lachmann, Lindenstr. 47a, D261 23 Oldenburg, Germany; Govinda Rajan, Rochelle Park, N.J.; Stephan Böhm, Bergisch Gladbach, Germany

[73] Assignee: Burkhard Lachmann, Oldenburg, Germany

[21] Appl. No.: 651,608

[22] Filed: May 22, 1996

[30] Foreign Application Priority Data

Jun. 2, 1995 [SE] Sweden ................. 9502032

[51] Int. Cl.$^6$ ................. A61M 16/00
[52] U.S. Cl. ................. 128/204.23; 128/204.18; 128/203.14; 128/716
[58] Field of Search ................. 128/203.14, 204.18, 128/204.23, 637, 671, 718, 719, 720, 725, 207.18, 203.12, 200.14, 716

[56] References Cited

U.S. PATENT DOCUMENTS

| | | | |
|---|---|---|---|
| 4,155,356 | 5/1979 | Venegal | 128/204.23 |
| 4,393,869 | 7/1983 | Boyarsky et al. | 128/204.23 |
| 4,462,398 | 7/1984 | Durkan et al. | 128/203.12 |
| 4,584,996 | 4/1986 | Blum | 128/207.18 |
| 4,841,974 | 6/1989 | Gumbrecht et al. | 128/635 |
| 4,917,080 | 4/1990 | Bayerlein | 128/204.23 |
| 5,103,814 | 4/1992 | Maher | 128/204.18 |
| 5,225,063 | 7/1993 | Gumbrecht et al. | 204/402 |
| 5,303,700 | 4/1994 | Weismann et al. | 128/204.18 |
| 5,388,575 | 2/1995 | Taube | 128/204.23 |

FOREIGN PATENT DOCUMENTS

| | | | |
|---|---|---|---|
| 0 671 180 | 9/1995 | European Pat. Off. | A61M 16/00 |
| 43 09 923 | 9/1994 | Germany | A61M 16/00 |
| 1 565 916 | 4/1980 | United Kingdom | A61M 16/00 |

OTHER PUBLICATIONS

"Open up the Lung and Keep the Lung Open", B. Lachmann, *Intensive Care Medicine*, vol. 18, 1992, pp. 319–321.

*Primary Examiner*—Vincent Millin
*Assistant Examiner*—V. Srivastava
*Attorney, Agent, or Firm*—Hill, Steadman & Simpson

[57] ABSTRACT

An arrangement for determining an opening pressure of a lung has a regulating unit which can deliver inspiration pulses to a patient's lung system, a blood gas analyzer for measuring the partial pressure of oxygen in the blood of the patient's circulatory system, and a control unit for determining an opening pressure based on the measured $P_a O_2$. When the measured $P_a O_2$ exceeds a predetermined threshold, the lung have opened sufficiently and a pressure value is correlated to the measured $P_a O_2$ and defined as the opening pressure.

7 Claims, 3 Drawing Sheets

RESPIRATORY SYSTEM FOR DETERMINING AN OPENING PRESSURE OF A LONG SYSTEM AND MAINTAINING THE LUNG SYSTEM OPEN

BACKGROUND OF THE INVENTION

1. Field of the Invention

The present invention relates to an arrangement for determining an opening pressure for a lung system of a subject, of the type having a regulating unit for delivering at least one predetermined inspiration pulse to the lung system.

2. Description of the Prior Art

In a healthy lung, air passes during inspiration through the airways and bronchi to the alveoli in the lungs. An exchange of gas occurs in the alveoli, whereby blood is oxygenated and carbon dioxide is simultaneously transferred to air in the alveoli. Gas containing carbon dioxide is extracted from the alveoli during expiration, permitting the entry of fresh air during the following inspiration. Since a healthy lung has a large compliance, i.e. a high flexibility, a relatively large volume of air can be inhaled in each breath without excessive increases in the pressure of air in the lungs.

As a result of injuries or disease, the function of the lung can be affected to such a degree that a life threatening condition could develop. For example the alveoli might collapse, thereby impairing or, worse, preventing the essential exchange of gas between air in the alveoli and blood in the minute capillaries of the lungs. The lungs can also have atelectatic regions which reduce the compliance so much that an insufficient volume of air is inhaled in each breath. Connection of the damaged lung to a ventilator/respirator may then be necessary to keep a patient alive until the damaged lung has healed. A ventilator/respirator can deliver a respiratory gas to the lungs with a pressure high enough to open the collapsed alveoli in order to provide a sufficient gas exchange. The necessity of a high pressure follows the Laplace Law, $P=2 y/r$, where P is pressure, y is surface tension and r is radius. A collapsed alveolus has a very small radius, whereas an open alveoli has a (relatively) large radius, thereby requiring a lower pressure to remain open or to be further inflated. In a healthy lung, the alveoli have a layer of natural surfactant. The natural surfactant has the ability of varying its surface tension, thereby for the healthy lung keeping even the minute alveoli open at fairly low pressures. In a pathological condition, such as ARDS (Acute Respiratory Distress Syndrome), however, the alveoli may be depleted of surfactant, resulting in a constant, high air-tissue surface tension in the alveoli. This, of course, makes it even more difficult to open the collapsed alveoli.

The importance of opening the lungs and keeping them open is further described in an article entitled "Open up the lung and keep the lung open" by B. Lachmann, Intensive Care Medicine (1992) 18:319–321. Air at a relatively high pressure must be supplied to the lungs in order to force the alveoli to open, whereas a much lower pressure is required to keep the alveoli open, once they have been opened properly. At the same time, the risk of lung trauma in forced respiration increases at higher pressures (barotrauma) and/or larger volumes of respiratory gas (volume trauma), especially if lung compliance is simultaneously poor. Another risk connected with excessive pressures is that the capillaries can be damaged by shear forces developing within the lung or can be compressed so that the blood cannot flow through the capillaries (over-distension), thereby also preventing a gas exchange. In the aforementioned article it is also noted that a sufficient partial pressure of oxygen $P_aO_2$ in the blood is a sign of the efficiency of gas exchange in the alveoli, i.e., a measure of the degree to which the lungs are open.

In published Swedish Application 501 560 a ventilator/respirator is described which can determine an opening pressure of a lung based on the relation between measured pressure values and volume values of a respiratory gas supplied to a patient. Basically the ventilator delivers a constant flow of respiratory gas during inspiration and the resulting pressure in the lung is measured and the volume of respiratory gas entering the lung is calculated. As long as the alveoli are collapsed the pressure will increase rapidly whereas the volume only increases slowly. As the alveoli open, the volume entering the lungs will increase more rapidly in relation to the pressure. The opening pressure is then determined by identifying the point of inflection in the P-V curve where the increase in volume becomes more rapid.

Although this procedure provides an opening pressure which can be used for determining the further treatment of the -patient, it is lacking somewhat insensitivity for determining an optimal opening pressure. For instance, there may be further inflection points in the P-V curve, which inflection points are not immediately identifiable as such. Further it does not guarantee that all collapsed alveoli have been opened properly.

SUMMARY OF THE INVENTION

It is an object of the present invention to provide an arrangement having a regulating unit for delivering at least on predetermined inspiration pulse to the lung system of a subject wherein an opening pressure can be determined at which at least a sufficient part of the lungs are open.

Such an arrangement is obtained in accordance with the invention having a blood gas analyzer connected to a circulatory system related to the lung system for measuring the partial pressure of oxygen ($P_aO_2$) and a control unit connected to the blood gas analyzer for determining the opening pressure based on the measured $P_aO_2$. The control unit operates the regulating unit dependent on the measured $P_aO_2$ to deliver respiratory gas to the lung system so as to ensure the lungs are open.

For the first time, it has been recognized that the measured $P_aO_2$ in itself can be used for determining the opening pressure for the lung system and as an indicator that the lungs are open, rather than being used only to insure that the patient receives a sufficient amount of oxygen. This provides the advantage that the opening pressure can be determined as the actual pressure at which at least a sufficient number of alveoli are forced open. It is possible to rely on the measured partial pressure of oxygen $P_aO_2$ as the exclusive or only parameter which is used to determine the opening pressure.

In one embodiment of the invention every $n^{th}$ inspiration pulse has an increased PIP, n being an integer equal to or larger than one and PIP being the peak inspiratory pressure. The inspiration pressure pulses are preferably square-shaped for providing an optimally efficient length of the inspiration period, i.e. the lungs are exposed to the peak pressure, PIP, during the entire inspiration period. Before increasing the PIP, the $PaO_2$ is measured. The control unit then determines the opening pressure as the first applied PIP at which the measured $P_aO_2$ exceeds a predetermined threshold. The inspiration period in this embodiment may be about 9 seconds.

It is of course possible to utilize a reversed sequence, i.e. a decrease in the PIP for every $n^{th}$ inspiration pulse. When the PIP is insufficient for opening the lung, the PIP of the preceding inspiration pulse is defined as the opening pressure. It should be noted that the applied pressures normally are sufficient for providing a life-sustaining supply of oxygen to the patient even during the determination of the opening pressure. The purpose of the procedure is to find an optimal opening pressure, which is used for determining the further treatment of the patient.

In a second embodiment of the invention a combination of the above sequences is utilized. First the PIP is increased every $n^{th}$ inspiration pulse, until an opening pressure is determined. Then the PIP is decreased every $m^{th}$ inspiration, m being an integer equal to or greater than one. The decreasing sequence continues until the measured $P_aO_2$ falls below the threshold. The preceding applied pressure is then the lowest opening pressure, or closing pressure, for an opened lung. In order to open the lung again, the first opening pressure must be applied again.

In a third embodiment a different inspiration pulse is utilized. Instead of controlling the pressure, the flow is controlled and a pressure gauge is used for measuring the pressure. This is similar to what is disclosed in the above identified Swedish Application 501 560, where a pressure-volume relation was used for determining the opening pressure. Such a relation can also be used in relation with this embodiment, whereas the measured $P_aO_2$ is used as the main prerequisite for determining when the lungs have opened up sufficiently. The $P_aO_2$ condition can be related to the determination of the opening pressure based on the pressure-volume relation.

If the patient is disconnected from the ventilator or if the condition of the lung changes (in particular deteriorates), the procedure for determining the opening pressure should be repeated. Spontaneous breathing of the patient can be allowed and supported if required during the determining procedure.

DESCRIPTION OF THE PREFERRED EMBODIMENTS

Figure 1:
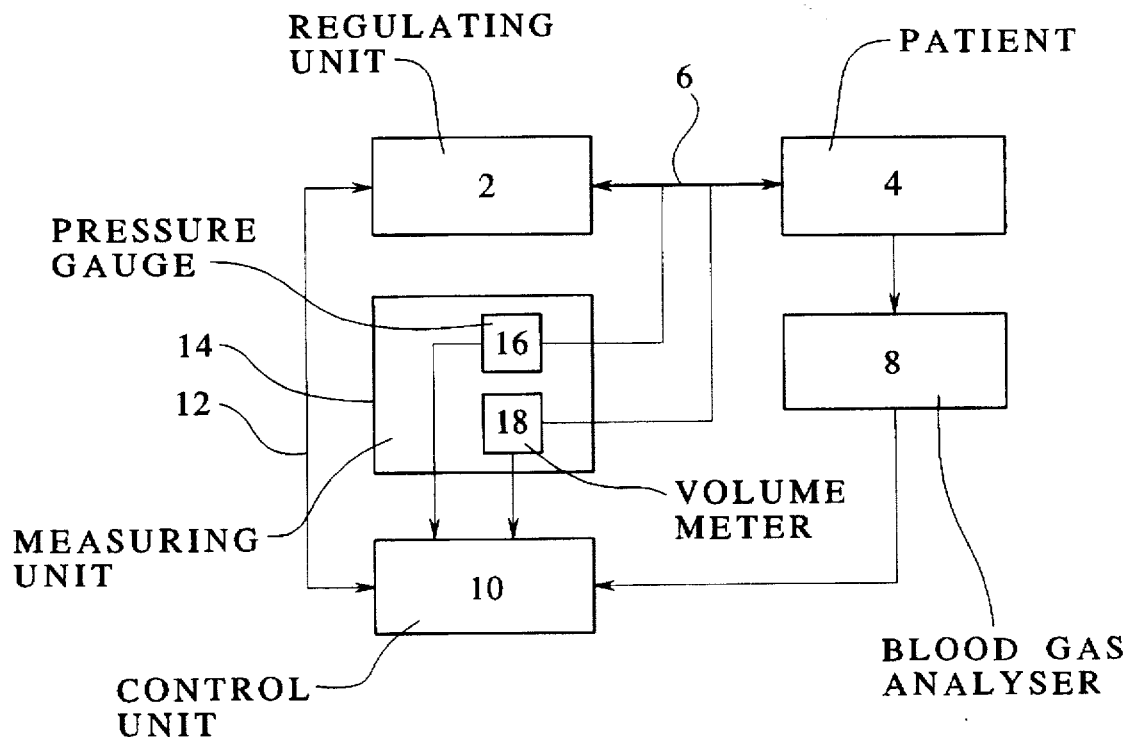
FIG. 1 schematically shows an arrangement according to the invention.

The principal elements of the inventive arrangement are schematically shown in FIG. 1. It should be noted that the functional blocks do not necessarily represent separate physical apparatus. A functional block may consist of several apparatus and some of the functional blocks may be incorporated in one apparatus. A regulating unit 2 is connected to a patient 4 via a gas delivery system 6. The regulating unit 2 can deliver a respiratory gas to the patient 4 and remove exhaled gas from the patient. The regulating unit 2 could basically be a modified ventilator/respirator of a known construction, such as Servo Ventilator 300, Siemens-Elema AB, Sweden. A blood gas analyzer 8 is connected to the circulatory system for measuring blood gases, in particular the partial pressure of oxygen ($P_aO_2$) in the patient 4. Blood gas analyzers suitable for this kind of analysis are described in U.S. Pat. Nos. 4,841,974 and 5,225,063.

The interconnection between the blood gas analyzer 8 and the circulatory system of the patient 4 can be made in several ways. For instance, a blood sample could be extracted from the circulatory system and analyzed in an apparatus outside the patient, or a probe could be inserted into the circulatory system for in vivo measurement of the blood gas. Also, measurements can be made at varying time intervals. The importance of measuring 'blood gases is the utilization of $P_aO_2$ as the primary parameter in the determining of an opening pressure for the lungs of the patient 4.

The blood gas analyzer 8 is connected to a control unit 10, which performs the determination of the opening pressure based inter alia measured $P_aO_2$. The control unit 10 is also connected to the regulating unit 2 via a signal line 12. The regulating unit 2 and the control unit 10 can exchange information between each other via the signal line 12. For example, the control unit 10 can send information to the regulating unit 2 when an opening pressure has been determined.

The arrangement also includes a measuring unit 14 which may be utilized for increasing the accuracy of the determination of the opening pressure. The measuring unit 14 is connected to the gas delivery system 6 and includes a pressure gauge 16 and a volume meter 18, both connected to the control unit 10. The volume meter 18 is basically a flow meter and an integrator for integrating the measured flow.

The utilization of the described arrangement will be described below in connection with the other figures.

The importance of opening the lung and keep the lung open has already been discussed above. A partially or completely collapsed lung will require a certain pressure to force the collapsed part open. It should be noted, however, that the opening pressure is not only a function of a peak pressure on the lungs, but also is affected by intrinsic and external PEEP (positive end expiratory pressure). Intrinsic PEEP can be created by selecting inspiration and expiration times in a certain relation to each other or by choosing a breathing rate which prevents the pressure in the lung to fall to atmospheric pressure at the end of expiration. The external PEEP is created by closing a valve, preventing gas from being exhaled, during the end of expiration. Further, it should also be noted that a certain amount of time can be required before the lungs will remain open during normal ventilation, i.e. the opening procedure usually requires more than a few breaths. In fact, it may require minutes before the lung adapts fully to the new ventilatory conditions.

In the present application the importance of the partial pressure of oxygen in the blood system of the patient for determining the opening pressure is recognized and used. There are several ways which the arrangement can utilize $P_aO_2$ in this way and some of these shall be described in more detail with reference to FIGS. 2–5.

Figure 2:
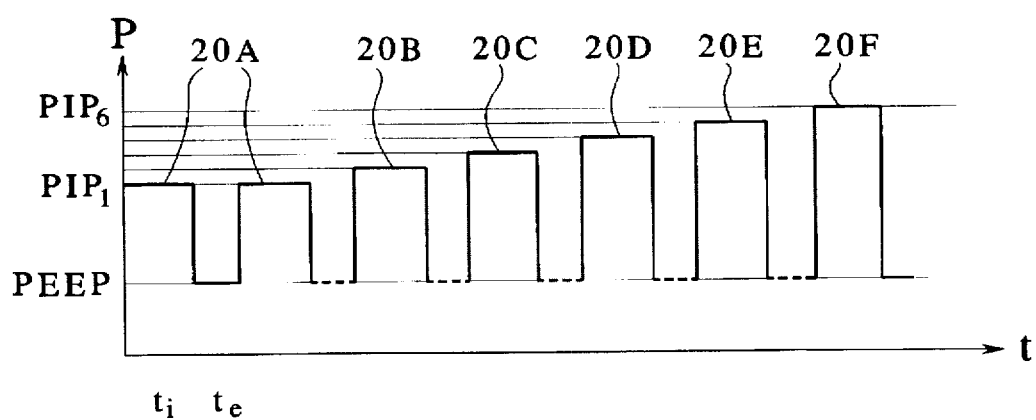
FIG. 2 shows a first inspiration pulse sequence which can be utilized for determining the opening pressure in the arrangement of FIG. 1.

FIG. 2 shows a sequence of inspiration pulses 20A–20F which the arrangement in FIG. 1 can deliver to the patient for determining the opening pressure. As shown in FIG. 2 the first inspiration pulse 20A is square-shaped and has a start pressure on PEEP level and a peak pressure of PIP, (peak inspiratory pressure). PEEP pressure is related to atmospheric pressure and is normally an over-pressure, but it can also be zero (i.e. equal to atmospheric pressure) or negative (in which case it is referred to as NEEP). When determining the opening pressure, however. PEEP pressure is always higher than or equal to zero. The PIP is the peak pressure during inspiration and should normally not exceed 60 cmH$_2$O. PIP may be between about 30–60 cm$_2$H 0 when determining the opening pressure in this manner. The first inspiration pulse 20A has in this case a PIP which is in the lower region of this interval. The first inspiration pulse 20A is then repeated one or several times. The following inspiration pulses 20B–20F have increasing peak pressures PIP$_2$-PIP$_6$. The increase can, for instance, be 4 cmH$_2$O after every n$^{th}$ inspiration pulse, n being the repetition number for each inspiration pulse 20A–20F. With a PIP$_1$, of 40 cmH$_2$O for the first inspiration pulse 20A the sixth inspiration pulse 20F will have a PIP$_6$ of 60 cmH$_2$O.

When the inspiration pulses 20A–20F are delivered to the patient, the P$_a$O$_2$ in the blood is measured by the blood gas analyzer 8. Since each inspiration pulse 20A–20F is repeated, there is time for improvements in the gas exchange in the alveoli to affect the P$_a$O$_2$ in the blood. If the first inspiration pulse 20A results in sufficient opening of the lung, the P$_a$O$_2$ will exceed a predetermined threshold, for example 350 mmHg. If not, the sequence of inspiration pulses 20B–20F then continues until the peak pressure eventually becomes so high, that the lungs open up sufficiently. For example, assume that the fourth inspiration pulse 20D is sufficient for opening up the lungs sufficiently. The measured P$_a$O$_2$ will then exceed the threshold of 350 mmHg. The peak pressure, PIP$_4$ of the fourth inspiration pulse 20D is then determined as the opening pressure for the lung, i.e., the opening pressure is 48 cmH$_2$O.

Figure 3:
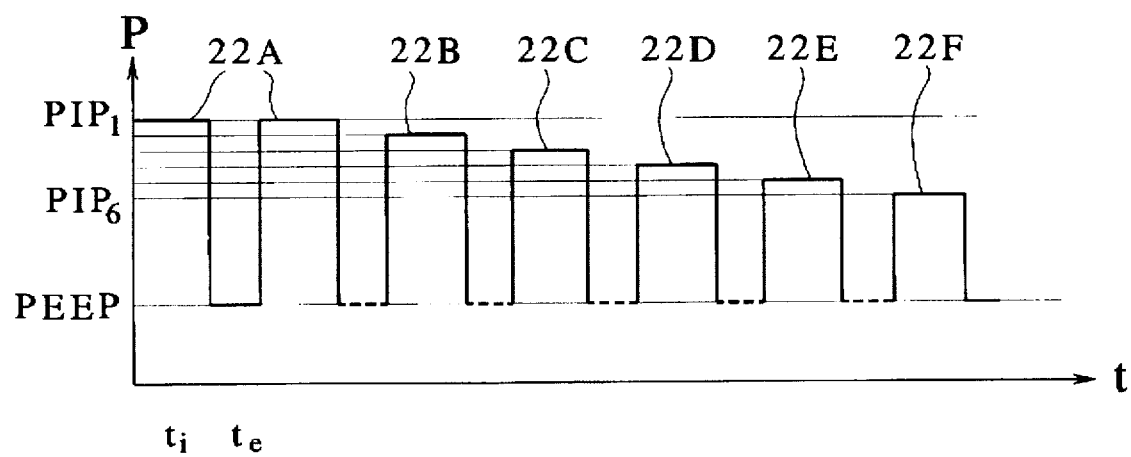
FIG. 3 shows a second inspiration pulse sequence which can be utilized for determining the opening pressure in the arrangement of FIG. 1.

In FIG. 3 a reversed sequence of inspiration pulses 22A–22F is shown. The first inspiration pulse 22A can have a PIP$_1$ of 55 or 60 cmH$_2$O, i.e., high enough to open the lungs in most cases. The first inspiration pulse 22A is repeated one or several times to allow for the P$_a$O$_2$-measurement to take place. If the measured exceeds the threshold, the second inspiration pulse 22B is applied for a number of consecutive times. The second inspiration pulse 22B has a PIP$_2$ which is lower than PIP$_1$. As long as the measured P$_a$O$_2$ exceeds the threshold, the sequence of inspiration pulses 22B–22F continues. When an inspiration pulse is insufficient for keeping the lungs open (measured P$_a$O$_2$ falls below the threshold), the preceding PIP is determined as the lowest opening pressure for the open lung. To reopen the lungs, one of the first inspiration pulses in the sequence must be applied again.

If the first inspiration pulse 22A is insufficient, another sequence of inspiration pulses must be selected. A new sequence can have the same peak pressure PIP$_1$-PIP$_6$, but an elevated PEEP, either external or intrinsic. Similarly, inspiration time t$_i$ and expiration time t$_e$ may be changed.

A combination of the inspiration pulse sequences in FIGS. 2 and 3 can also be utilized. The opening pressure should then first be determined with a sequence according to FIG. 2 and the lowest opening pressure or closing pressure could then 35 be determined by applying the sequence of FIG. 3.

Figure 4:
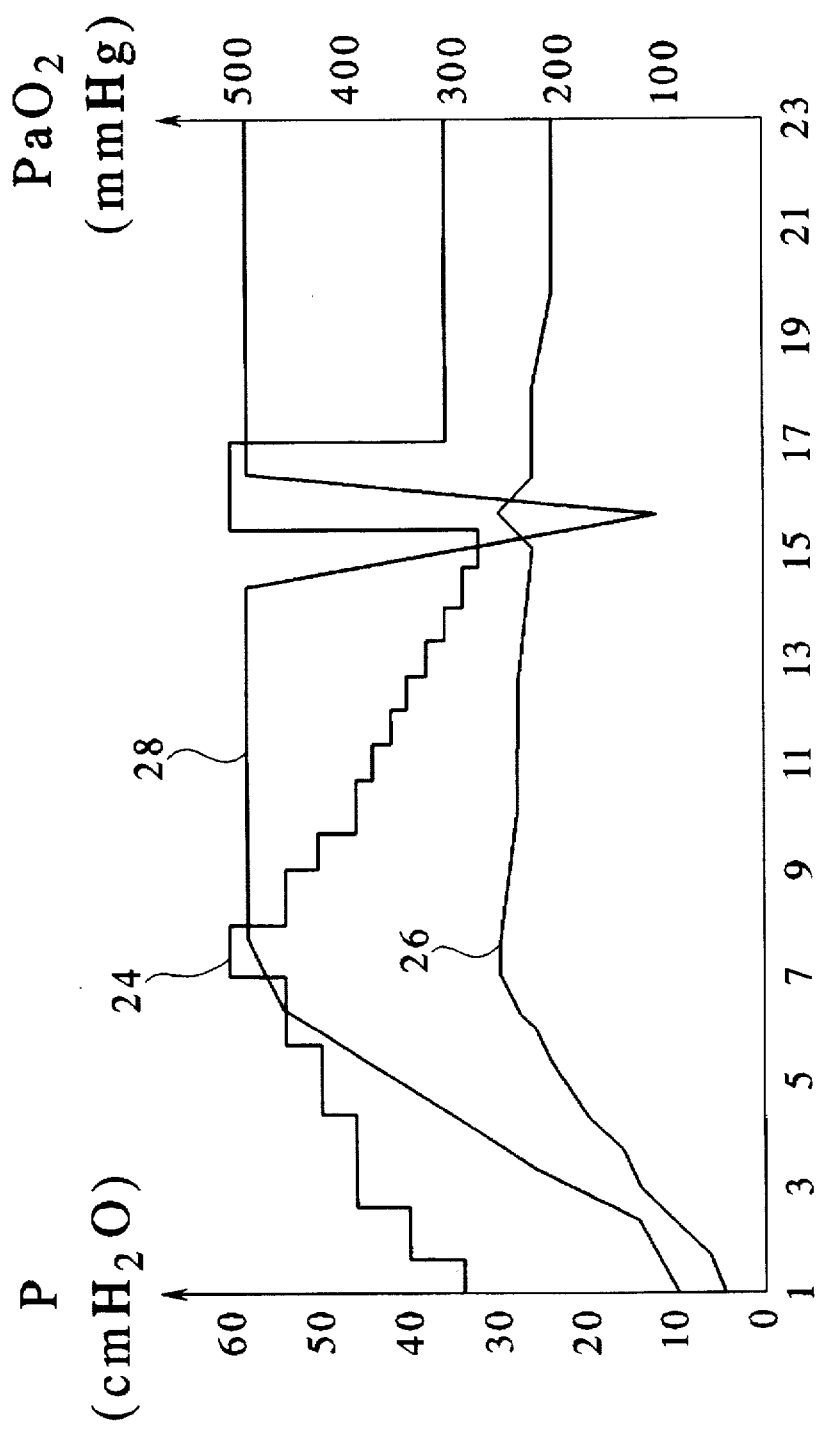
FIG. 4 diagrammatically shows the inventive determining procedure.

The procedures for determining the opening pressure, described in this application, have also been tested on pigs. The result of such an experiment is shown in FIG. 4. The pig's lungs are first depleted of surfactant by lung lavage i.e., the lungs are rinsed with a liquid. After the lavage, the lungs will respond as a patient having ARDS. On the horizontal line the experiment time is depicted, on the left vertical line measured pressure (corresponding to applied PEEP and PIP) and on the right vertical line measured P$_a$O$_2$. It should be noted that the diagram does not show individual breaths, but the variation of certain parameters during the experiment. The diagram will be described in three parts, reflecting the arrangement of the experiment. The first part reflects events up to about 8 minutes, the second part between 8 and 15 minutes and the third part the remaining time. The times given here are for this particular experiment and could vary in the order of minutes or hours in other experiments.

A first curve 24 shows the PIP during the experiment. In the first part, the PIP increases at intervals and each PIP-level is maintained for one or two minutes. A second curve 26 shows the measured PEEP, which also increases in the first part, thereby basically keeping the pressure difference PIP-PEEP constant. The second curve 26 is smoother than the first curve 24. This is due to the fact that a combination of external and intrinsic PEEP is utilized in this case. Therefore, the measured PEEP does not increase in stages. A third curve shows measured P$_a$O$_2$. For this experiment the threshold to be reached by the measured P$_a$O$_2$ was set at 500 mmHg. A steady increase in measured P$_a$O$_2$ can be seen until it finally, after about 8 minutes, reaches the threshold. The PIP has by this time been increased to 60 cmH$_2$O and PEEP has been increased to almost 30 cmH$_2$O. The PIP of 60 cmH$_2$O is the opening pressure.

The first curve 24, i.e., PIP, is then decreased in stages, as shown in the second part of the diagram. Following Laplace's law, described above, a lower pressure is required to keep the lung open. In this second part of the experiment, the lowest pressure keeping the lungs open is sought. As indicated by the second curve 26, however, PEEP is not decreased as much, resulting in a decreasing pressure difference PIP-PEEP. For some time the measured P$_a$O$_2$ remains constant, as shown by the third curve 28, confirming that the lung is kept open even though the PIP is decreased.

In the third part of the diagram, the lungs are opened up again by applying the same PIP and PEEP which opened up the lungs in the first part. The measured P$_a$O$_2$ increases rapidly up to 500 mmHg and the applied PIP and PEEP can then be set at the lowest opening pressure. This will keep the lungs open until they have improved.

Figure 5:
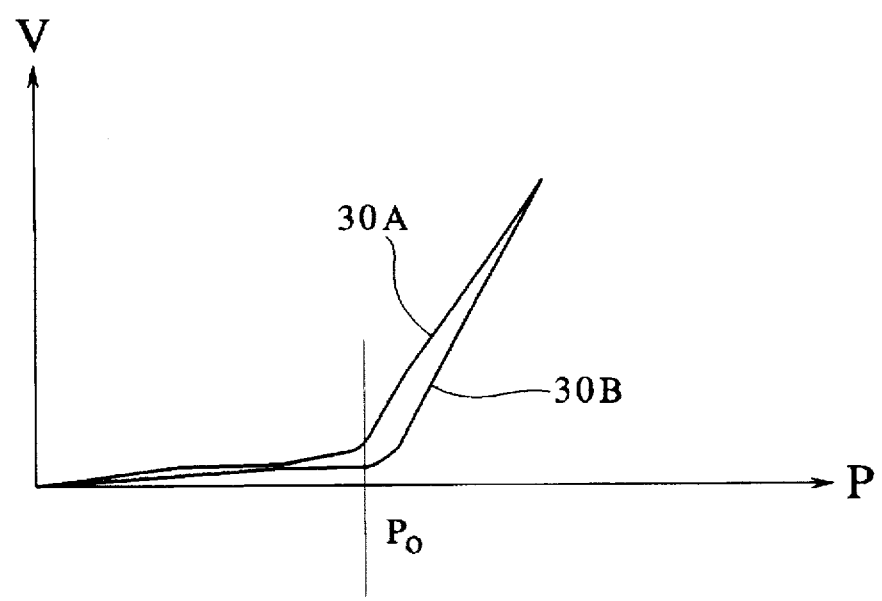
FIG. 5 shows a pressure-volume diagram which can be utilized for determining the opening pressure in the arrangement of FIG. 1.

In FIG. 5, a third embodiment of utilizing the arrangement of FIG. 1 is described. Basically, FIG. 5 shows a pressure volume diagram similar to the one in the above described Swedish Application 501 560, but with the further improvement of utilizing measured P$_a$O$_2$ as the relevant factor in order to determine the opening pressure. In principle, the calculated opening pressure is a relevant opening pressure only if it can achieve a sufficient opening of the lung, i.e., achieve a measured P$_a$O$_2$ which exceeds the threshold. Since the pressure-volume curve is obtained by applying a defined constant flow, this flow could be varied in order to vary the increase in the pressure to obtain new curves, from which new opening pressures can be calculated. The first calculated opening pressure which can be correlated to a sufficient opening of the lung is chosen as the relevant opening pressure, or the optimal opening pressure. By applying a flow ramp instead of a constant flow, a more predominant inflection point should be achievable. In the diagram a first curve 30A and a second curve 30B have been shown in the P-V-diagram. The inflection points have been identified and the higher is chosen as the Opening pressure P$_o$ since it could be correlated to a sufficient opening of alveoli. Since flow is controlled and the necessary opening pressure is not reached until the end of the inspiratory period, it would be preferable first to determine an opening pressure and then to apply this pressure in pressure control mode for several breaths.

Other pressure or flow pulses can be delivered to the lungs in order to determine the opening pressure. The relevant concept of the present application is to determine the opening pressure based on the measured $P_aO_2$, and in particular to correlate the opening pressure to a sufficient opening of the lung, which correlates to a $P_aO_2$ which exceeds a predetermined threshold.

Although modifications and changes may be suggested by those skilled in the art, it is the intention of the inventors to embody within the patent warranted hereon all changes and modifications as reasonably and properly come within the scope of their contribution to the art.

We claim as our invention:

1. A respiratory apparatus comprising:

respiratory gas regulating means for delivering at least one predetermined inspiration pulse of respiratory gas to the lung system of a subject;

blood gas analyzer means, interacting with the circulatory system of the subject, for measuring a partial pressure of oxygen in the blood of said circulatory system and for emitting a measured signal indicative of said partial pressure of oxygen; and control means, supplied with said measured signal, for determining an opening pressure of said lung system based on said measured signal and for controlling said regulating unit for altering said at least one predetermined inspiration pulse of respiratory gas as necessary to maintain said lung system open.

2. A respiratory apparatus as claimed in claim 1 wherein said at least one predetermined inspiration pulse has a predetermined peak pressure, and wherein said control means comprises means for altering said peak pressure as necessary for maintaining said lung system open.

3. A respiratory apparatus as claimed in claim 2 wherein said regulating means comprises means for delivering a plurality of respiratory gas inspiration pulses to the lung system with every $n^{th}$ inspiration pulse having an increased peak pressure, n being an integer greater than or equal to one, and wherein said control means comprises means for determining the opening pressure as a last peak pressure at which said measured signal exceeds a predetermined threshold.

4. A respiratory apparatus as claimed in claim 2 wherein said regulating means comprises means for delivering a plurality of respiratory gas inspiration pulses to the lung system with every $m^{th}$ inspiration pulse having a decreased peak pressure, m being an integer greater than or equal to one, and wherein said control means comprises means for determining the opening pressure as a last peak pressure at which said measured signal exceeds a predetermined threshold.

5. A respiratory apparatus as claimed in claim 2 wherein said regulating means comprises means for emitting a plurality of respiratory gas inspiration pulses with said peak pressure being increased at each $n^{th}$ inspiration pulse, wherein said control means comprises means for comparing said measured signal to a predetermined threshold and for controlling said regulating means to stop increasing said peak pressure of said inspiration pulses when said measured signal exceeds said predetermined threshold, wherein said regulating means comprises means for thereafter decreasing the peak pressure of every $m^{th}$ inspiration pulse, and wherein said control means comprises means for identifying when said measured signal falls below said predetermined threshold, n and m each being an integer greater than or equal to one, and wherein said control means comprises means for determining said opening pressure as a first peak pressure at which said measured signal exceeded said predetermined threshold, and said control means further comprising means for determining a lowest opening pressure as a last peak pressure at which said measured signal remained above said predetermined threshold.

6. A respiratory apparatus as claimed in claim 1 wherein said at least one predetermined respiratory gas inspiration pulse has a start and an end, and said respiratory apparatus further comprising measuring means for measuring at least one respiratory gas parameter between said start and said end, and for emitting a gas parameter measured signal, and wherein said control means comprises means for determining said opening pressure dependent on said gas parameter measured signal and said measured signal indicative of the partial pressure of oxygen.

7. A respiratory apparatus as claimed in claim 6 wherein said measuring means comprises:

a volume meter which determines a respiratory gas volume supplied to said lung system between said start and said end; and a pressure gauge which determines a respiratory gas pressure substantially at the lung system, and wherein said control means comprises means for determining said opening pressure dependent on said respiratory gas volume, said respiratory gas pressure, and said measured signal indicative of the partial pressure of oxygen.

* * * * *